United States Patent [19]

Fuchs

[11] 4,102,176
[45] Jul. 25, 1978

[54] METHOD AND APPARATUS FOR MEASURING INTENSITY OF PEENING OF SMALL SURFACES

[75] Inventor: Henry O. Fuchs, Stanford, Calif.

[73] Assignee: Metal Improvement Company, Inc., Teaneck, N.J.

[21] Appl. No.: 792,189

[22] Filed: Apr. 29, 1977

[51] Int. Cl.² ............................................. G01N 33/00
[52] U.S. Cl. ............................................. 73/12; 73/104
[58] Field of Search ................ 73/12, 88 R, 104, 37.5, 73/7; 85/37

[56] References Cited

U.S. PATENT DOCUMENTS

| | | | |
|---|---|---|---|
| 1,328,591 | 1/1920 | Rushton | 308/163 |
| 1,937,086 | 11/1933 | Kaplan | 85/37 |
| 2,350,440 | 6/1944 | Almen | 73/12 |
| 2,465,002 | 3/1949 | Aller | 73/37.5 |
| 3,511,081 | 5/1970 | Worthen et al. | 73/37.5 |

Primary Examiner—Jerry W. Myracle
Attorney, Agent, or Firm—Arthur Frederick

[57] ABSTRACT

The peening intensity test member is a factory assembled unit comprising a base structure having opposite faces and a test element secured to one of the faces of the base structure, the test element being removable from the base structure after peening for measurement of the amount of its deformation.

The method of measuring the peening intensity comprises the steps of peening the exposed surface of the test element while secured to the base structure. Thereafter the test element is removed from the base structure and allowed to deform as a result of the compressive stress layer produced in the exposed surface of the test element by peening. The test element is then held on a surface of a measuring device so that a space is formed as a result of its deformation between the test element and the adjacent surface of the device. A fluid under a low pressure is metered to the space and the rate of leakage from the space is measured, such leakage rate being a function of the amount of deformation.

27 Claims, 14 Drawing Figures

METHOD AND APPARATUS FOR MEASURING INTENSITY OF PEENING OF SMALL SURFACES

This invention relates to shot peening, and more specifically, to the method of and apparatus for measuring intensity of peening in the Almen scale of small surface areas of workpieces which areas may be partially shielded, such as small fillets, and the roots of gear teeth or threads.

BACKGROUND OF THE INVENTION

As is fully explained in the U.S. Patent to Smith, No. 3,695,091, dated Oct. 3, 1972, shot peening the surface of a workpiece beyond "saturation" (overpeening) produces no beneficial results and is wasteful use of peening material and apparatuses. To achieve peening "saturation" and to avoid peening beyond the "saturation" point or overpeening, as well as achieving the correct degree of peening, means have been devised for the nondestructive measuring of peening intensity. One such device is the Almen strip which consists of a thin flat strip of the A, C or N type and having a size 7.62 centimeters (3 inches) long, 1.9 cm (¾ of an inch) wide and a thickness of about 0.78 mm (0.031 inch) to about 2.38 mm (0.0938 inch). Another device for measuring the peening intensity of the surfaces of small diameter holes and which utilizes the Almen strip, is disclosed in the aforesaid Smith patent. In both these methods and devices the strip is subjected to shot peening for a specified time with the same combination of size of shot, material of the shot, and striking velocity of the shot as is to be used in the peening of workpieces such as a structural or machine part. After exposure of the strip to the shot, the amount of deformation or curvature of the strip is measured, and this curvature resulting from the impaction of peening shot constitutes a measure of the intensity of the stresses set up in the peened surface (or the extent of the compressive layer produced in the metallic surface) and hence, is a measure of peening intensity. The Almen test provides a means of measuring the results of a peening operation and, therefore, after several such tests and the recording of the exposure times, serves as a basis for establishing the treatment time for a particular workpiece.

It has been found that the Almen test strip, while satisfactory for relatively large exposed surfaces, is unsatisfactory for the measurement of peening intensity in small areas which may also be difficult to reach with the "rain" of shot.

It is therefore an object of the present invention to provide a method of and apparatus for measuring intensity of peening on small area surfaces in terms of the Almen scale.

It is another object of this invention to provide a method and apparatus for measuring peening intensity which is cheaper and more reliable than the use of Almen strips.

SUMMARY OF THE INVENTION

Accordingly, the present invention contemplates a method of measuring intensity of peening of relatively small surfaces, such as the roots of gears and threads and fillets, of workpieces, which method comprises the first step of peening the exposed surface of a test member secured on a base structure. Thereafter, the peened test element is removed from its base structure and allowed to deform as a result of the compressive layer or stresses produced in the surface of the test element by the peening operation. The deformed test element is held to the surface of a measuring device so that a space is formed between the test element and the adjacent surface of the measuring device. A fluid under pressure is next introduced into the space between the test element and the measuring device at a controlled rate. The leakage from the space is then measured, the leakage being a function of the amount of deformation of the test element.

The test member, according to this invention, comprises a base structure and a test element of relatively thin, flat configuration removably secured to the base structure so that one surface of the test element is exposed for peening. The base structure may be disk-shaped, a cube or prism in shape while the test element is preferably generally of washer-like, disk or of three-pointed star configuration.

The measuring device, according to this invention, comprises a housing forming a chamber therein and having means for securing the deformed test element to the housing so that a space is formed as a result of its deformation between the test element and the adjacent surface of the housing. A conduit means is provided for connecting the housing chamber with a source of fluid under pressure. A restricted passage means for communicating the housing chamber with the space between the test element and housing and thereby passing controlled amounts of pressurized fluid, as for example air, from the housing chamber into the space, is also provided in the device. A pressure measuring means is connected to measure the pressure in the chamber, the pressure being a function of the flow rate through the restricted passage means and, in turn, is a function of the rate of leakage from the space between the housing and test element and, hence, a measure of the amount of deformation of the test element. The pressure measuring means may be provided with an Almen scale so that pressure is indicated in Almen scale units.

BRIEF DESCRIPTION OF THE DRAWINGS

The invention will be more fully understood from the following description when considered in connection with the accompanying drawings in which.

DESCRIPTION OF THE PREFERRED EMBODIMENT

Figure 1:
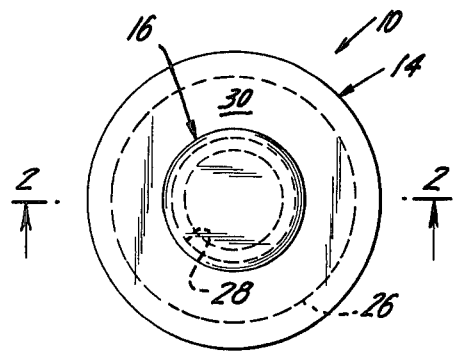
FIG. 1 is a plan view of a test member according to a first embodiment of this invention.
Figure 2:
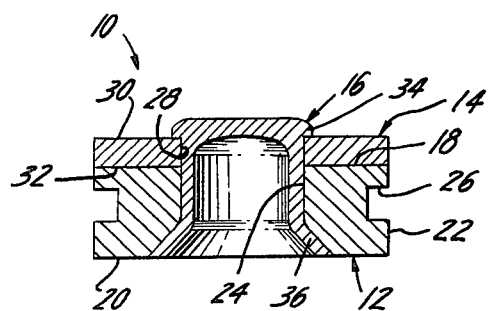
FIG. 2 is a cross-sectional view taken substantially along line 2—2 of FIG. 1.

Now referring to the drawings and more particularly FIGS. 1 and 2, the reference number 10 generally designates a peening intensity test member which may be utilized in the method of measuring the peening intensity of small surfaces in the Almen scale.

The test member 10 comprises a base structure 12 (see FIG. 2) and a test element 14 which is of flat, relatively thin configuration and removably secured to base structure 12 by a rivet 16.

The base structure 12, as best shown in FIG. 2, may be of a disk-shape having opposite faces 18 and 20 and a peripheral surface 22. An axial hole 24 is provided in base structure 12 so as to extend through opposite faces 18 and 20. To hold the base structure 12 to a support (not shown) for shot peening, a recess 26 is provided in peripheral surface 22 to receive a retaining means (not shown), such as an O-ring, split ring or retaining pins.

The test element 14 is preferably of washer-like configuration having a diameter substantially the same as base structure 12 and a hole 28 therein of substantially the same diameter as axial hole 24 of base structure 12. The test element also has opposite planar surfaces 30 and 32 and is flat and free of residual stresses. To measure peening intensity of small surface areas, such as shaft fillets and roots of gears and threads, or the like, the test element is considerably smaller than an Almen strip. For example, the diameter of test element 14 may be only 10 mm (0.39 inches) in outside diameter and about 4 mm (0.17 inches) in inside diameter. The test element 14 may be, however, of approximately the same thickness as the Almen strip, namely, between 0.78 mm (0.031 inch) and 2.38 mm (0.0938 inch) and of the same material and hardness as the Almen strip of the A, C or N type depending upon the intensity of peening desired, or may be of aluminum or titanium material.

In the assembly of test member 10 into a unitary assembly, test element 14 is positioned with its surface 32 in abutment against face 18 of base structure 12 and with the hole 28 aligned with hole 24 of the base structure. The rivet 16 is then inserted in registered holes 24 and 28 and is deformed at 34 and 36 to respectively grip test element 14 along its inner peripheral edge and base structure 12. The rivet 16 functions to secure the test element 14 and base structure together as a unit thereby eliminating the time formerly required to secure an Almen strip on its supporting block.

Figure 3:
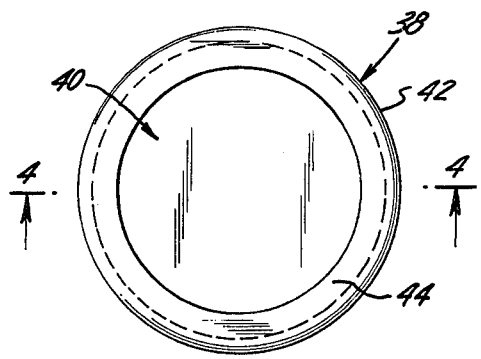
FIG. 3 is a plan view of a test member according to a second embodiment of the present invention.
Figure 4:
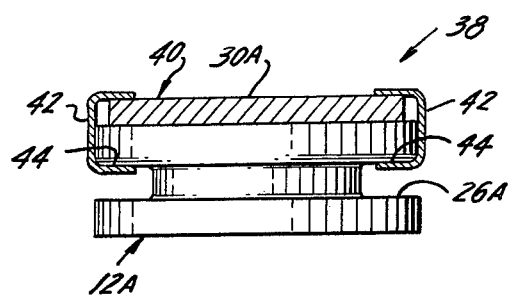
FIG. 4 is a view in cross-section taken substantially along line 4—4 of FIG. 3.

In FIGS. 3 and 4 is shown an alternative test member 38 which may be employed to measure peening intensity according to this invention. The test member 38 differs principally from test member 10 in the manner in which the test element and base structure are held together. In view of the similarities between test member 10 and 38, the parts of test member 38 corresponding to like parts of test member 10 will be designated by the same number but with the suffix A added thereto.

The test member 38 comprises a test element 40 which is diskshaped rather than of washer-like configuration as is test element 14 and a base structure 12A. The base structure 12A differs from base structure 12 in that it is a solid member which does not have a central hole for a rivet as has base structure 12 of test member 10. It has a recess 26A in peripheral surface 22A which is similar to recess 26 of base structure 12, but of greater depth than recess 26. A clamping ring 42 of channel-shape in cross-section is disposed to embrace the outer peripheral edge of test element 40 and the lip 44 formed by recess 26A in base structure 12A. The clamping ring 42, similar to rivet 16, functions to join test element 14 and base structure 12A into a unitary assembly and with a substantial portion of the surface 30A of the test element exposed for peening. The recess 26A also functions to receive a retaining means as explained with respect to recess 26 of test member 10.

In use of test member 10 (FIGS. 1 and 2) or test member 38 (FIGS. 3 and 4), the test member is held in a suitable holder (not shown); as for example, a socket having spring loaded retaining pins or ring. The test member is then subjected to shot peening for the time, at the shot velocity, and with the size and type shot contemplated for peening the surface of a workpiece (not shown). This "rain" of shot against the exposed surface 30 or 30A of test element 14 or 40, sets up stresses in surface 30 or 30A which are substantially proportional to that produced in the surface of the workpiece when subjected to the same size, type, velocity of shot, and for the same duration. After peening of test member 10 or 38, the rivet 16 or clamping ring 42 is removed to permit test element 14 or 40 to be separated from its associated base structure. In the case of test member 14, rivet 16 might be removed by drilling or grinding away crimped portion 36 of the rivet. In the case of test member 38, the clamping ring 42 might be pried from recess 26A by means of any suitable tool (not shown). The test element 14 or 40, when separated from its associated base structure and after peening of its surface 30 or 30A, deforms or bends to a convex shape by reason of the stresses set up in the surface 30 or 30A (see FIGS. 6 and 8). This deformation or deflection will amount to about 0.02 mm or about 0.001 inch. The deformed test element 14 or 40 may then be placed respectively, as shown in FIGS. 5 to 10, on an intensity measuring device 50 or 50A according to this invention.

Figure 5:
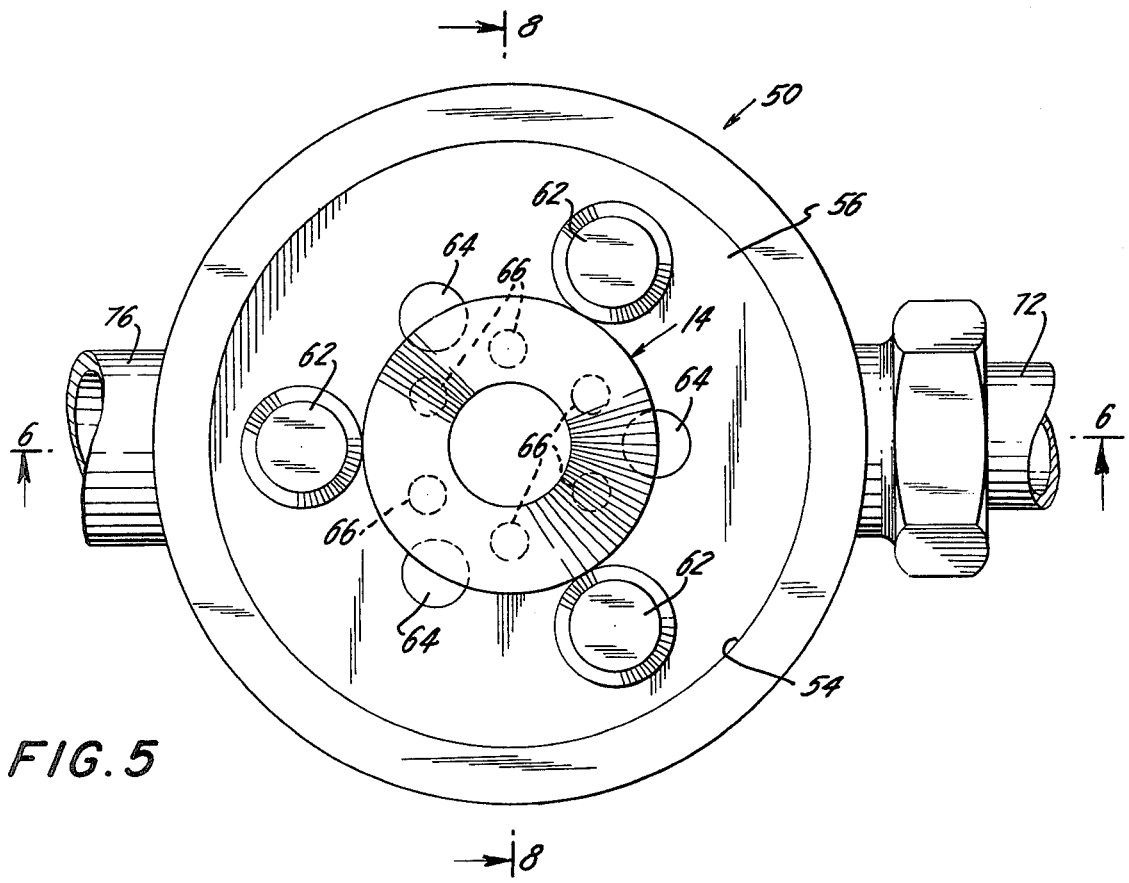
FIG. 5 is a fragmentary plan view of the measuring device according to this invention.
Figure 6:
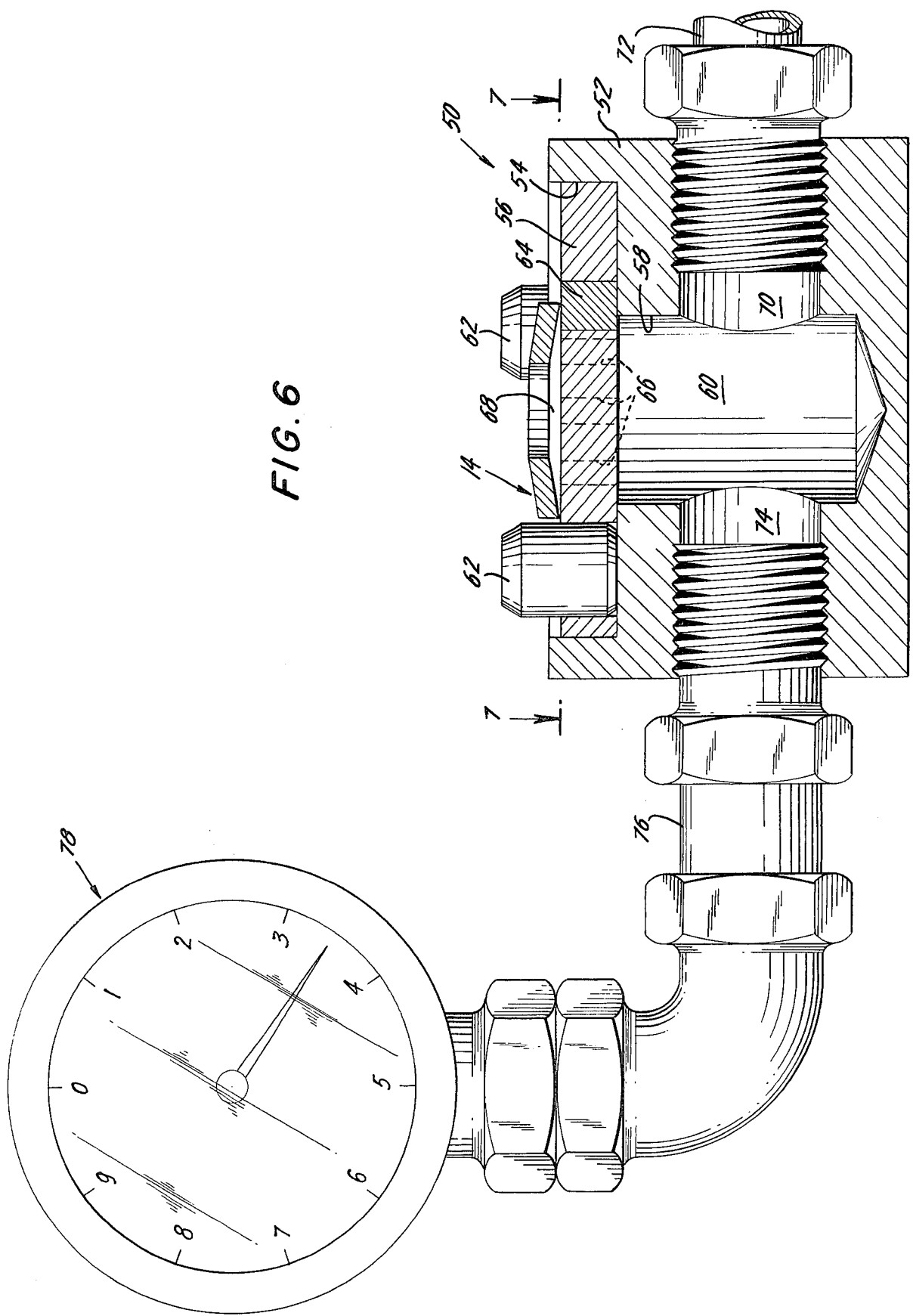
FIG. 6 is a view in cross-section taken along line 6—6 of FIG. 5 with a gage in elevation shown attached to the measuring device.
Figure 7:
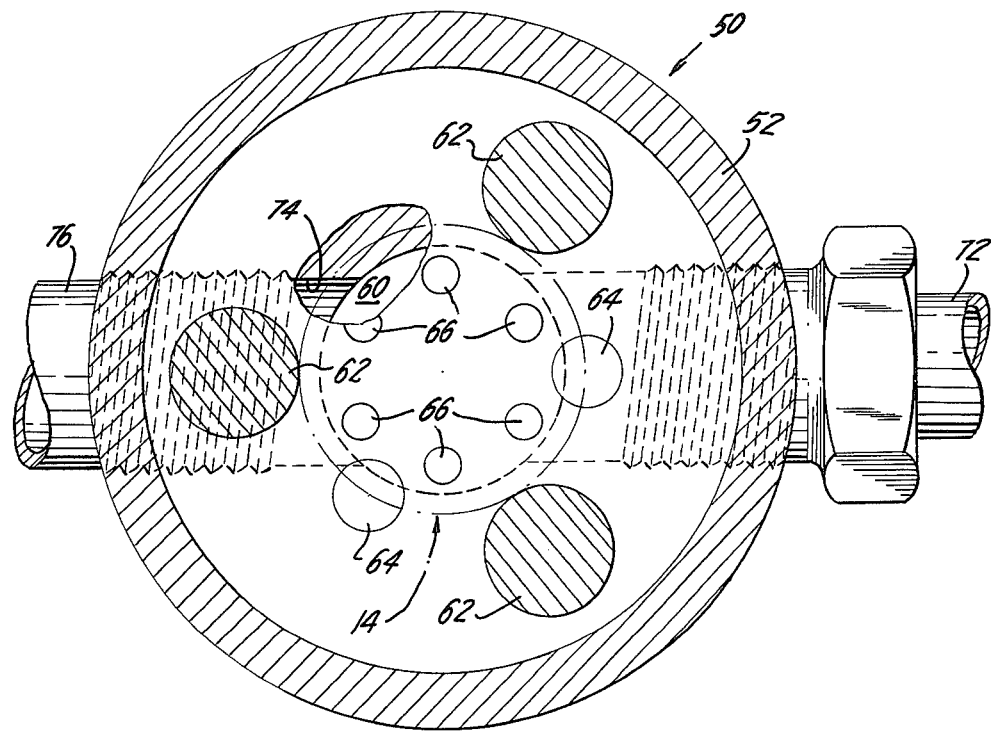
FIG. 7 is a cross-sectional view taken substantially along line 7—7 of FIG. 6 with part broken away for illustration purposes.
Figure 8:
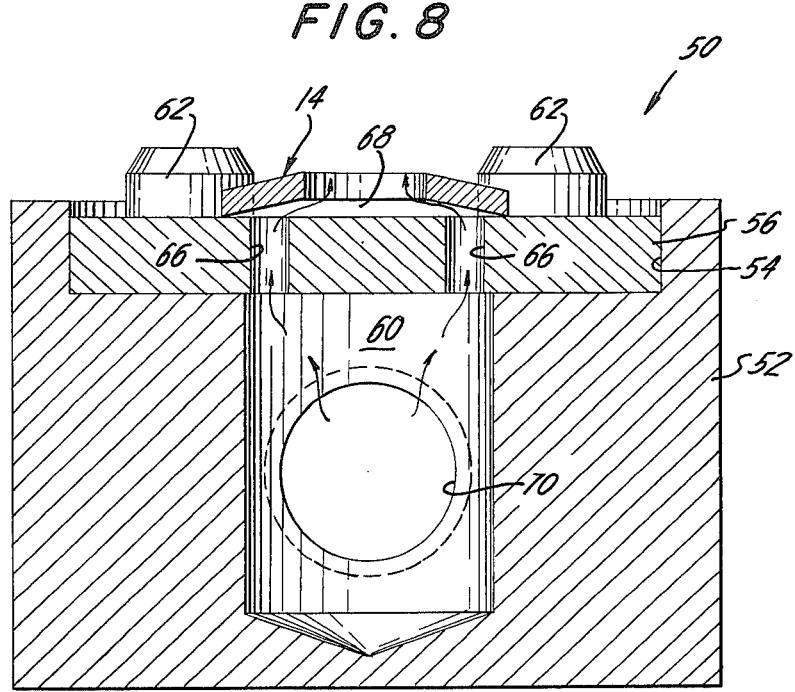
FIG. 8 is a view in cross-section taken substantially along line 8—8 of FIG. 5.

The intensity measuring device 50 comprises a cylindrical block or housing 52 which has a circular recess 54 in one end thereof and in which recess is secured a circular plate 56 of nonmagnetic material, such as brass. The plate 56 defines with the walls of a blind axial bore 58 to a chamber 60. As best shown in FIGS. 5 and 7, plate 56 carries three circumferentially, equi-spaced pins 62 which are spaced so as to receive therebetween a deformed test element 14. To secure test element 14 to the surface of housing plate 56, a plurality of permanent magnets 64 are arranged in plate 56 to partly bridge the peripheral edge of test element 14. Disposed along an imaginary circle concentric with, but of smaller diameter than the peripheral edge of test element 14, is a plurality of spaced orifices or holes 64 in plate 56. As best shown in FIG. 8, each of the holes 66 (preferably six in number) extend through plate 56 to communicate at one end with chamber 60 and at the other end with a space 68 which is formed by the concavity of test element 14 and the adjacent surface of plate 56. The flow area of holes 66 is relatively small to form a restriction and thereby permits control of flow of pressurized fluid, such as air, from chamber 60 to space 68 and the maintenance of a fluid pressure in chamber 60 in accordance with the fluid loss from space 68. The use of 6 or more circumferentially spaced orifices 66 is preferred because the greater the number, the greater is their function of averaging the small irregularities in the deflection or deformation of test elements 14. To supply chamber 60 with fluid under relatively low pressure, housing 52 is provided with a threaded bore 70 to which is connected one end of a pressure supply pipe 72, the other end being connected to a source of fluid under pressure, such as a compressor or pressurized reservoir. Diametrically opposite threaded bore 70 is a second threaded bore 74 in which a pipe 76 is turned to communicate chamber 60 with a pressure gage 78.

In the function or operation of intensity measuring device 50, a deformed test element 14 is placed between posts 62 with the concave side adjacent the surface of plate 56 so that space 68 is formed therebetween. Fluid under a carefully regulated, relatively low pressure is flowed into chamber 60 via supply pipe 72. The fluid under pressure flows, from chamber 60 through orifices or holes 66, into space 68. From space 68 the fluid escapes from space 68 via hole 28 or 28A or possibly past the outer peripheral edge of the test element 14 or 14A, if irregularities of deformation occur at the outer peripheral edge. The rate of escape or leakage depends upon the size of space 68 and hence the degree of deformation of test element 14. The pressure in chamber 60 will be maintained at a value commensurate with the leakage flow rate and therefore pressure gage 78 will indicate such pressure level or value. Since the pressure value is a function of leakage, and leakage in turn, is a function of the degree of deformation of test element 14, pressure gage 78 may, as shown, be calibrated to indicate pressure conditions in terms of the Almen scale. The magnets 64 are of sufficient strength to hold test element 14 against the surface of plate 56 under the fluid pressure tending to lift the test element from the plate.

Figure 9:
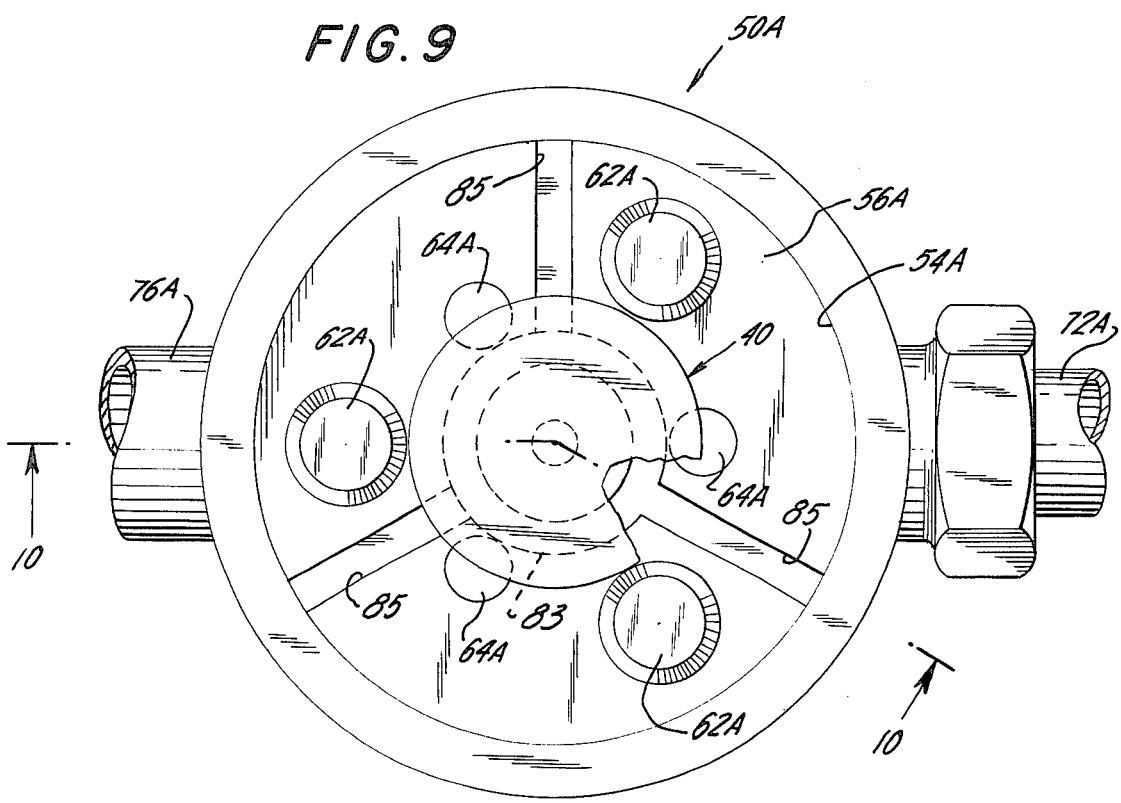
FIG. 9 is a plan view of an alternative measuring device according to this invention and particularly useable in conjunction with the test element shown in FIGS. 3 and 4.
Figure 10:
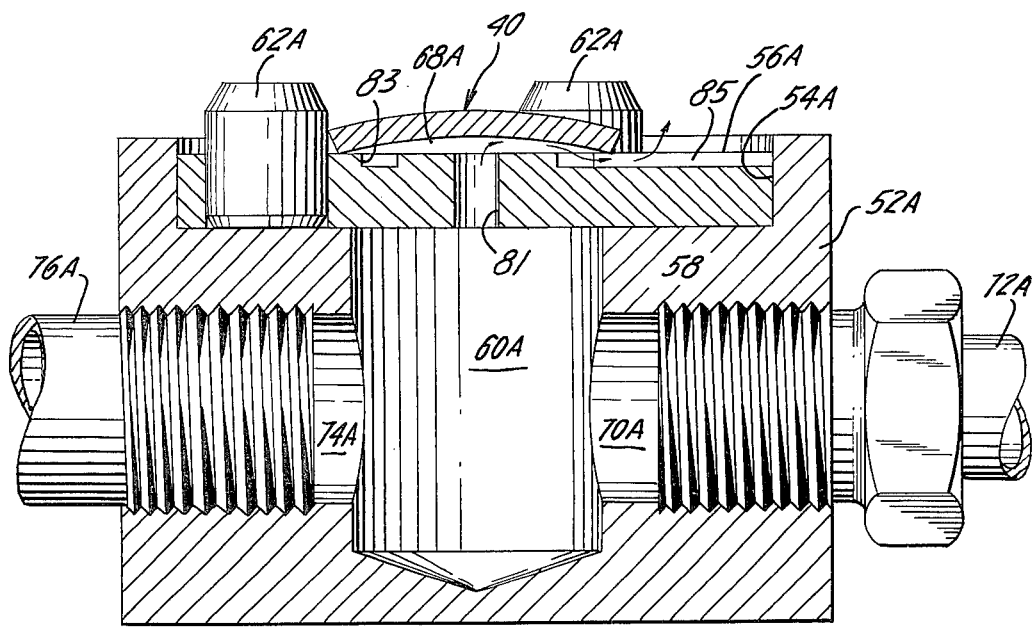
FIG. 10 is a view in cross-section taken substantially along line 10—10 of FIG. 9.

In FIGS. 9 and 10 is shown intensity measuring device 50A which is suitable for use in conjunction with test element 40. Since measuring devices 50 and 50A are very similar, like parts of device 50A will have the same reference number as the corresponding part of device 50 but with the suffix A added thereto.

The measuring device 50A is identical to measuring device 50 except for the construction of plate 56A. The plate 56A has a central opening 81 which communicates chamber 60A with the space 68A between the concave surface of disk-shaped test element 40 and the adjacent surface of plate 56A. To provide a leakage flow path for the low pressure fluid in space 68A, plate 56A has an annular groove 83 concentric with hole 81 and of smaller diameter than the test element and three radial channels or troughs 85 extending outwardly from annular groove 83. This leakage flow path is best illustrated in FIG. 10.

Figure 11:
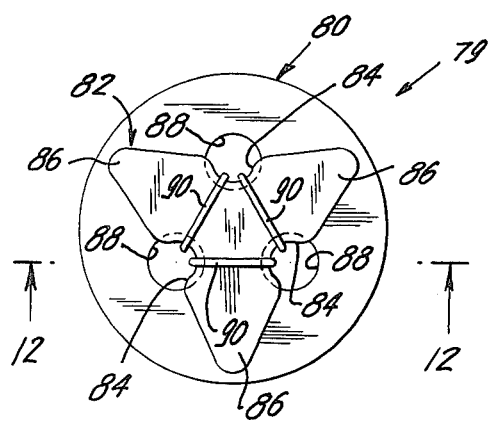
FIG. 11 is a plan view of a test member, according to a third embodiment of the invention.
Figure 12:
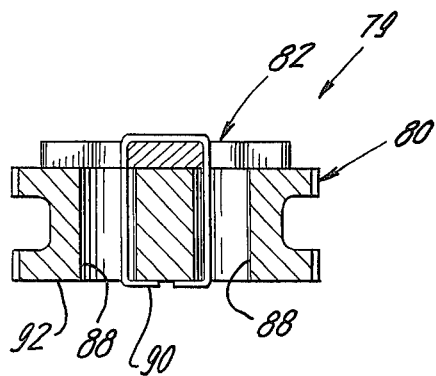
FIG. 12 is a cross-sectional view taken substantially along line 12—12 of FIG. 11.

In FIGS. 11 and 12 is shown a test member 79, according to a third embodiment of this invention. The test member 79 differs from test members 10 and 38 principally in that the test element is of generally triangular shape, or of three pointed star shape, rather than being washer or disk-shaped in construction and also differs in the manner in which the test element is secured to a base structure.

The test member 79 comprises, as shown, a base structure 80 to which is removably secured a test element 82 of flat, generally triangular or star-shape and having three arcuate recesses 84 to form three points or fingers 86. The test element is of the same material and is of substantially the same small overall size as test element 14 and 40 of test members 10 and 38. A three-finger or pointed test element is preferred since three points determine a plane and such construction insures that a deformed test element has three points of contact with magnets 64 of measuring device 50.

The base structure 80 has three spaced holes 88 which, when test element 82 is properly positioned on base structure 80, are substantially coaxial with the axis of arcuate recesses 84.

The test element 82 is secured to one face 89 of base structure 80 by a plurality of clips 90. As best shown in FIG. 12, each of these clips engage a finger 86 and extends over adjacent recesses 84 and through holes 88 on opposite sides of the associated finger, the ends of clips 90 being folded against the underface 92 of base structure 80.

Figure 13:
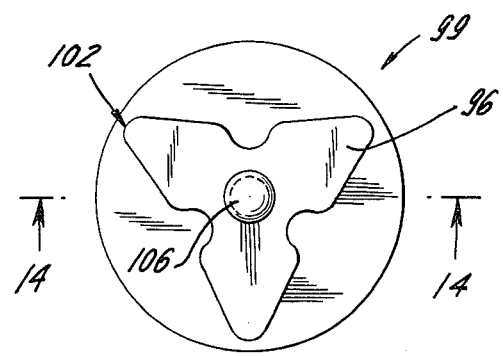
FIG. 13 is a test member, in plan view, according to a fourth embodiment of the present invention.
Figure 14:
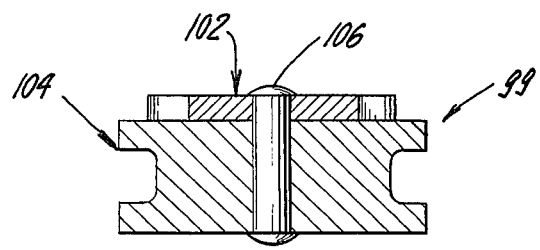
FIG. 14 is a cross-sectional view taken along line 14—14 of FIG. 13.

In FIGS. 13 and 14 is shown a test member 99, according to a fourth embodiment of the present invention. The test member 99 is similar to test member 79 with the principal difference being the manner in which the test member is secured to its associated base structure.

The test member 99 has a test element 102, almost identical to test element 82 of test member 79, which is secured to a base structure 104 by a centrally located rivet 106. Since the test element is held to one face of base structure 104 by a rivet, the base structure has a central hole for rivet 106 and does not have the holes 88 which are in the base structure 80 of test member 79.

The method of using test members 79 and 99 is the same as described with respect to test members 10 and 38. More specifically, after peening the surface of the test elements 82 or 102, it is removed from its associated base and is placed on intensity measuring device 50 with its concave side facing the surface of plate 56 of the device so as to define therebetween a space, similar to space 68, described with respect to test element 40. The test element 82 is also positioned so that each of its fingers overlie a hole 66. The measuring device 50 is suitable for use with test elements 82 and 102 because the gap between the next adjacent fingers 86 and 96 provides the leakage path from the space beneath the test elements. The device 50 may be modified to the extent of providing an appropriate number and location of throttling holes 66 for properly conducting fluid into the space between test elements 82 or 102 and the surface of plate 56.

The advantage that test elements 82 and 102 have over the washer-like test element 14 and the disk-shaped test element 40, is that the fingers 86 and 96 of test elements 82 and 102 function to increase the flexibility of the test elements. This increased flexibility minimizes the inherent characteristic of increased resistance to deformation or deflection as the degree of deformation increases. Thus, the deflection or deformation of test elements 82 and 102 more accurately indicates the relatively high stresses set up in the peened surface than would test elements 14 and 40.

It is believed now readily apparent that the present invention provides a method of and apparatus for measuring peening intensity for small surface areas which is more accurate and reliable than methods employing Almen strips because (i) the preferred round shape of the test element has no preferred direction of deformation as in the rectangular Almen strip where lengthwise and crosswise curvatures occur, and (ii) fluid pressure is more sensitive to deformation so that more accurate readings can be obtained than is possible by mechanical measurement of an Almen strip which has compound curvatures. The invention provides a relatively cheap test member since the test member can be a machine-made and assembled device which thus eliminates the manual labor and the time required for securing an Almen strip to its support block.

While a plurality of embodiments of the invention and method have been illustrated and described in detail, it is expressly understood that the invention is not limited thereto. Various changes can be made in the arrangement of parts or steps without departing from the spirit and scope of the invention as the same will now be understood by those skilled in the art.

What is claimed is:

1. A method of measuring the peening intensity of metal surfaces of workpieces comprising the steps of:
    (a) peening the exposed surface of a test element secured on a base structure and having at least one opening therethrough;
    (b) removing the peened test element from its base structure and allowing it to deform as a result of the compressive layer produced in the surface of the test element by peening;
    (c) holding the deformed test element to the surface of a measuring device so that a space is formed between the test element and the adjacent surface of the measuring device;
    (d) introducing at a controlled rate fluid under pressure to said space; and
    (e) measuring the leakage of said fluid from the space at least some of which is through said one opening, which leakage is a function of the amount of deformation.

2. The method of claim 1 wherein said fluid is air at a relatively low pressure.

3. The method of claim 1 wherein leakage measurement is indicated on an Almen scale.

4. The method of claim 1 wherein the step of introducing, at a controlled rate, fluid under pressure to said space includes first passing pressurized fluid into a chamber and constricting the flow of pressurized fluid from the chamber into the space and wherein said measuring step includes the passing of pressurized fluid from the chamber into a pressure gage.

5. The method of claim 1 wherein holding the test member to the measuring device includes magnetism.

6. A peening intensity test member comprising:
    (a) a base structure having at least one flat surface;
    (b) test element of relatively thin configuration and having opposite flat surfaces of substantially the same size as the flat surface of said base structure;
    (c) said test element being disposed with one flat surface thereof in abutment against said flat surface of the base member; and
    (d) securing means for removably connecting said test element to said base structure so that substantially all of the surface of the test element opposite from said one surface thereof is exposed for peening.

7. The apparatus of claim 6 wherein said test element has a washer-like configuration.

8. The apparatus of claim 7 wherein said base structure has a cylindrical projecting portion receivable in the said hole in the test member.

9. The apparatus of claim 7 wherein said test element is secured to the base structure by clamping means disposed to grip the outer periphery of the test member.

10. The apparatus of claim 9 wherein said clamping means is an annular clip U-shaped in cross-section.

11. The apparatus of claim 6 wherein said test element is disk-shaped.

12. The apparatus of claim 6 wherein said test element has a three pointed star configuration.

13. The apparatus of claim 6 wherein said base structure has a circumferential recess in the periphery.

14. The apparatus of claim 6 wherein said securing means is a rivet passing through an opening in the test element and a registered hole in the base structure.

15. A peening intensity test member comprising
    (a) a base structure having opposite faces and a peripheral surface;
    (b) a washer-shaped test element having opposite faces of substantially the same size of at least one face of the base structure and disposed with one of its faces abutting said one face of the base structure;
    (c) said test element having an outer peripheral edge surface and a hole therethrough defining an inner peripheral edge surface; and
    (d) clamping means disposed to engage one of said peripheral edge surfaces of the test member to secure the test member to the base structure and dimensioned to leave a substantial amount of the face of the test element opposite its abutting face exposed for peening.

16. The apparatus of claim 15 wherein said base structure is disk-shaped.

17. The apparatus of claim 16 wherein said clamping means is a clip means gripping the outer peripheral edge surface of the test element and the peripheral surface of the base structure.

18. The apparatus of claim 15 wherein said clamping means has a hole in register with the hole in the test element and wherein the clamping means is a rivet extending through the registered holes.

19. The apparatus of claim 15 wherein said base member has in the face receiving the test element a cylindrical projection of a diameter slightly smaller than the diameter hole in said test member so as to be receivable in said hole.

20. The apparatus of claim 19 wherein said base structure has a recess means in the peripheral surface and wherein said clamping means includes a clip means for gripping the outer peripheral edge surface of the test element and the recess means in the base structure thereby connecting the test element and base structure into a unitary assembly.

21. The combination with a test element of relatively thin, flat configuration deformed by peening, an intensity measuring device comprising
    (a) a housing forming a chamber therein;
    (b) conduit means connecting said chamber to a source of pressurized fluid;
    (c) mechanical holding means for securing the test element, which has deformed as a result of peening and has been removed from the test member, to the housing so that a space is defined between the test element and adjacent housing surface;
    (d) passage means communicating the housing chamber with said space to pass pressurized fluid to the latter; and
    (e) pressure sensing and measuring means connected to the housing to sense and measure the pressure in said housing chamber which pressure is a function of the rate of fluid leakage from the space by reason of the deformation of the test element.

22. The apparatus of claim 21 wherein the holding means includes magnetic means.

23. The apparatus of claim 22 wherein the passage means comprises a plurality of restrictive passages.

24. The apparatus of claim 22 wherein said holding means comprises a plurality of spaced projections which abut the periphery of the test element and a plurality of permanent magnets arranged in the housing adjacent the test element.

25. The apparatus of claim 21 wherein said housing is provided with a second passage means for providing a fluid leakage flow path from said space to the atmosphere.

26. The apparatus of claim 25 wherein said passage means is a single hole.

27. The apparatus of claim 21 wherein said passage means is a plurality of circumferentially spaced holes in the housing.

* * * * *